United States Patent [19]

Schwamborn et al.

[11] Patent Number: 4,721,523
[45] Date of Patent: Jan. 26, 1988

[54] HERBICIDAL AGENTS CONTAINING PHOTOSYNTHESIS-INHIBITING HERBICIDES IN COMBINATION WITH CARBAMATE DERIVATIVES

[75] Inventors: Michael Schwamborn, Cologne; Gerhard Heywang, Bergisch-Gladbach; Karlfried Dickoré, Leverkusen; Winfried Lunkenheimer, Wuppertal; Carl Fedtke, Cologne, all of Fed. Rep. of Germany

[73] Assignee: Bayer Aktiengesellschaft, Leverkusen, Fed. Rep. of Germany

[21] Appl. No.: 774,270

[22] Filed: Sep. 10, 1985

[30] Foreign Application Priority Data

Sep. 13, 1984 [DE] Fed. Rep. of Germany ....... 3433541

[51] Int. Cl.$^4$ ............................................. A01N 43/707
[52] U.S. Cl. .............................................. 71/93; 71/90; 71/91; 71/92; 71/105; 71/106; 71/111; 71/118; 71/120
[58] Field of Search ..................................... 71/93, 106

[56] References Cited

U.S. PATENT DOCUMENTS 4,420,326 12/1983 Bell ......................................... 71/93
4,427,440 1/1984 von der Osten et al. ............. 71/94

OTHER PUBLICATIONS

Heywang et al. I, "Carbamic Acid Esters, etc.," (1984) CA 100:174291u (1984).
Heywang et al. II, "Carbamic Acid Esters, etc.," (1984) CA 101:23004x (1984).
Heywang et al. III, "Carbamic Acid Esters, etc.," (1984) CA 102:5723x (1985).
Stephenson et al., "Phytotoxic Interactions, etc.," (1980) 92:192549e (1980).
Ditgens et al., "Herbicide from Triazinome, etc.," (1984) CA 101:38482a (1984).

*Primary Examiner*—Glennon H. Hollrah
*Assistant Examiner*—A. A. Owens
*Attorney, Agent, or Firm*—Sprung Horn Kramer & Woods

[57] ABSTRACT

A herbicidal composition comprising a herbicidally effective among of
(a) a photosynthesis-inhibiting herbicidally active compound, and
(b) a synergistically effective amount of a carbamate derivative of the formula (II)

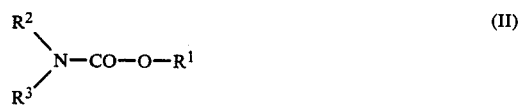

in which
$R^1$ is alkyl, halogenoalkyl, alkenyl, alkinyl or optionally substituted phenyl,
$R^2$ is alkyl, halogenoalkyl, alkoxy, alkenyl, optionally substituted cycloalkyl or optionally substituted cycloalkylalkyl,
$R^3$ is hydrogen, $-CO-OR^4$, $-CO-CO-OR^5$ or $-CO-CO-NR^6R^7$,
$R^4$ is alkyl, alkenyl, alkinyl or optionally substituted phenyl,
$R^5$ is alkyl, alkenyl or alkinyl, and
$R^6$ and $R^7$ each independently is hydrogen, alkyl or alkenyl.

8 Claims, No Drawings

HERBICIDAL AGENTS CONTAINING PHOTOSYNTHESIS-INHIBITING HERBICIDES IN COMBINATION WITH CARBAMATE DERIVATIVES

The present invention relates to new herbicidal synergistic active compound combinations consisting of known photosynthesis-inhibiting herbicides on the one hand and certain widely known carbamate derivatives on the other hand.

It has already been disclosed that certain herbicides, such as, for example, 4-amino-6-tert.-butyl-3-methylthio-1,2,4-triazin-5-one; 1-amino-3-(2,2-dimethylpropyl)-6-(ethylthio)-1,3,5-triazine-2,4-dione; 6-chloro-2-ethylamino-4-isopropylamino-1,3,5-triazine or 1-methoxy-1-methyl-3-(3,4-dichlorophenyl)-urea, have photosynthesis-inhibiting properties (compare, for example, Carl Fedtke, Biochemistry and Physiology of Herbicide Action, Springer Verlag, 1982). However, the disadvantage of these herbicidal compounds is that not always all of the broad-leaved and graminaceous weeds occurring are completely affected, or that some species of cropped plants are partially damaged when correspondingly high amounts are applied.

It has been found that the new active compound combinations consisting of
(a) a photosynthesis-inhibiting active compound (herbicide) and
(b) a carbamate derivative of the general formula (II) (synergist)

(II)

in which
$R^1$ represents alkyl, halogenoalkyl, alkenyl, alkinyl or optionally substituted phenyl,
$R^2$ represents alkyl, halogenoalkyl, alkoxy, alkenyl, optionally substituted cycloalkyl or optionally substituted cycloalkylalkyl and
$R^3$ represents hydrogen or the grouping $-CO-OR^4$, $-CO-CO-OR^5$ or $-CO-CO-NR^6R^7$, wherein
$R^4$ represents alkyl, alkenyl, alkinyl or optionally substituted phenyl,
$R^5$ represents alkyl, alkenyl or alkinyl and
$R^6$ and $R^7$ are identical or different and represent hydrogen, alkyl or alkenyl, have a particularly high herbicidal activity.

Surprisingly, the herbicidal activity of the active compound combinations according to the invention is substantially greater than the sum of the actions of the individual active compounds. In particular, the widely known carbamate derivatives of the general formula (II) do not have an intrinsic herbicidal action when the usual amounts are applied, but effect an increase in the herbicidal action of the photosynthesis-inhibiting active compounds. The synergistic effect found here is thus completely unexpected and surprising.

Since the synergistic effect also concerns those weeds which are only insufficiently damaged or are not affected at all when the photosynthesis-inhibiting active compounds used are applied by themselves in the usual amounts, the synergistic active compound combinations according to the invention represent a valuable enrichment of the art.

Photosynthesis-inhibiting active compounds which may be mentioned for the active compound combinations according to the invention are preferably the following of the general formulae (I-A) to (I-J):

(A) triazinone derivatives of the formula

(I-A)

in which
$X^1$ represents amino, optionally substituted alkylideneamino or alkyl with 1 or 2 carbon atoms;
$X^2$ represents alkylthio with 1 or 2 carbon atoms, alkyl- or dialkyl-amino with in each case 1 or 2 carbon atoms in each alkyl part, or alkyl with 1 to 4 carbon atoms; and
$X^3$ represents tert.-butyl which is optionally substituted by halogen, or optionally substituted phenyl;

(B) triazinedione derivatives of the formula

(I-B)

in which
$X^4$ represents amino, optionally substituted alkylideneamino or alkyl with 1 or 2 carbon atoms;
$X^5$ represents alkylthio with 1 or 2 carbon atoms, alkyl- and dialkylamino with in each case 1 or 2 carbon atoms in each alkyl part, or alkyl with 1 to 4 carbon atoms; and
$X^6$ represents alkyl with 1 to 6 carbon atoms or optionally substituted phenyl;

(C) triazine derivatives of the formula

(I-C)

in which
$X^7$ represents chlorine, alkoxy or alkylthio with in each case 1 or 2 carbon atoms;
$X^8$ represents alkylamino with 1 to 4 carbon atoms in the alkyl part; and
$X^9$ represents alkyl which has 1 to 4 carbon atoms and is optionally substituted by cyano;

(D) urea derivatives of the formula

(I-D)

in which $X^{10}$ represents optionally substituted phenyl, benzothiazolyl or optionally substituted thiadiazolyl;

$X^{11}$ represents hydrogen or methyl;

$X^{12}$ represents methyl; and $X^{13}$ represents hydrogen, alkyl with 1 to 4 carbon atoms, alkoxy with 1 or 2 carbon atoms or alkinyl with 2 to 4 carbon atoms;

(E) carboxanilide derivatives of the formula $$X^{14}-CO-NH-X^{15} \quad \text{(I-E)}$$

in which $X^{14}$ represents alkyl with up to 6 carbon atoms, alkoxy with 1 to 4 carbon atoms, alkenyl with 2 to 4 carbon atoms or cycloalkyl with 3 to 6 carbon atoms; and $X^{15}$ represents optionally substituted phenyl;

(F) uracil derivatives of the formula

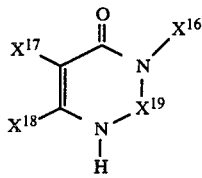
(I-F)

in which $X^{16}$ represents alkyl with 1 to 6 carbon atoms or cycloalkyl with 5 to 7 carbon atoms;

$X^{17}$ represents halogen; and $X^{18}$ represents alkyl with 1 or 2 carbon atoms, or $X^{17}$ and $X^{18}$ together represent an optionally substituted alkylene chain or an optionally substituted fused-on benzene ring; and $X^{19}$ represents the —CO— or —SO$_2$— group;

(G) biscarbamate derivatives of the formula

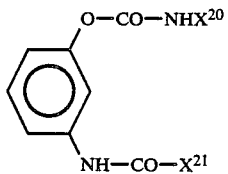
(I-G)

in which $X^{20}$ represents alkyl with 1 to 4 carbon atoms or optionally substituted phenyl; and $X^{21}$ represents alkoxy with 1 to 4 carbon atoms or dialkylamino with 1 or 2 carbon atoms in each alkyl part;

(H) pyridiazinone derivatives of the formula

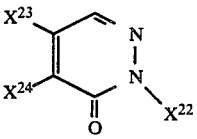
(I-H)

in which $X^{22}$ represents optionally substituted phenyl;

$X^{23}$ represents amino or alkylamino or dialkylamino with in each case 1 or 2 carbon atoms in each alkyl part; and $X^{24}$ represents halogen;

(J) hydroxybenzonitrile derivatives of the formula

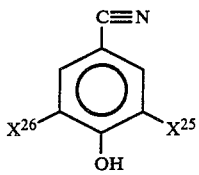
(I-J)

in which $X^{25}$ represents halogen; and $X^{26}$ represents halogen.

The following photosynthesis-inhibiting active compounds of the general formulae (I-A) to (I-J) are particularly preferred:

(A) triazinone derivatives of the formulae

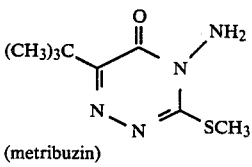
(I-A-1)

(metribuzin)

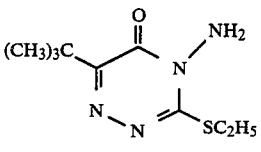
(I-A-2)

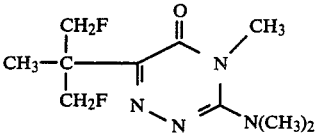
(I-A-3)

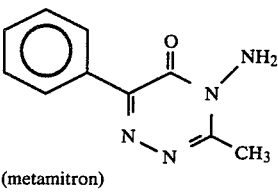
(I-A-4)

(metamitron)

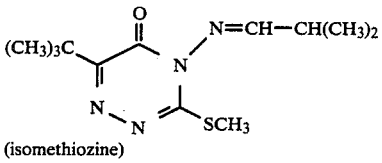
(I-A-5)

(isomethiozine)

(B) triazinedione derivative of the formula

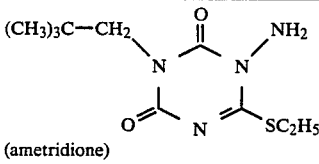
(I-B-1)

(ametridione)

(C) triazine derivatives of the formulae

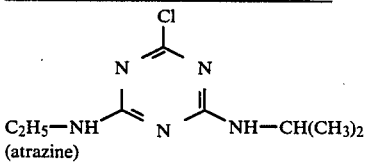
(I-C-1)

(atrazine)

(I-C-2) ametryne (I-C-3) atraton (I-C-4) cyanazine (I-C-5) prometon (I-C-6) prometryne (I-C-7) propazine (I-C-8) simazine (I-C-9) simeton (I-C-10) simetryne (I-C-11) terbutryne (I-C-12) trietazine (D) urea derivatives of the formulae (I-D-1) linuron (I-D-2) methabenzthiazuron (I-D-3) isoproturon (I-D-4) benzthiazuron (I-D-5) buthiuron (I-D-6) buturon (I-D-7) chlorbromuron (I-D-8) chloroxuron -continued
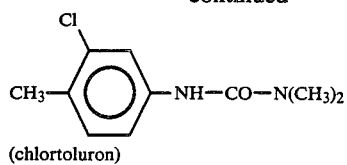
(chlortoluron) (I-D-9)
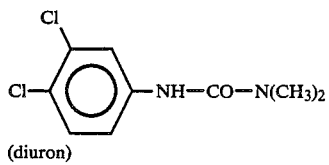
(diuron) (I-D-10)
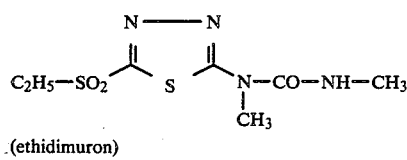
(ethidimuron) (I-D-11)
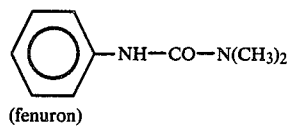
(fenuron) (I-D-12)
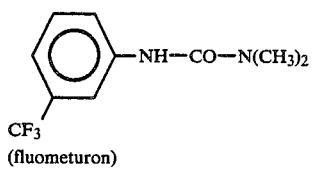
(fluometuron) (I-D-13)
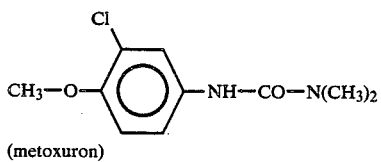
(metoxuron) (I-D-14)
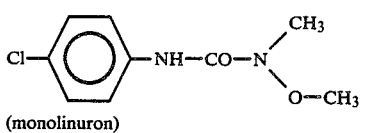
(monolinuron) (I-D-15)
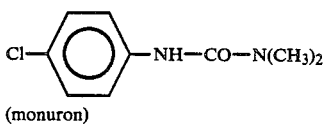
(monuron) (I-D-16)
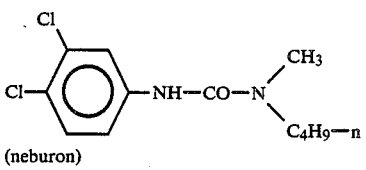
(neburon) (I-D-17)
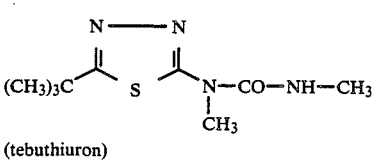
(tebuthiuron) (I-D-18)
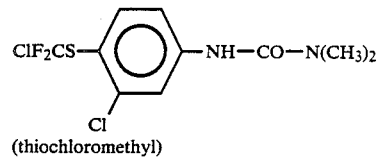
(thiochloromethyl) (I-D-19)
(E) carboxanilide derivatives of the formulae
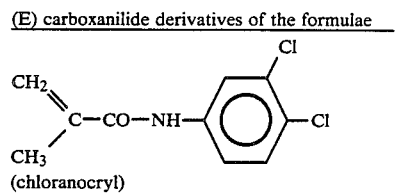
(chloranocryl) (I-E-1)
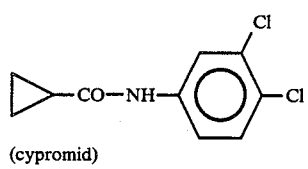
(cypromid) (I-E-2)
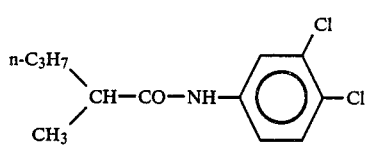
(Karsil) (I-E-3)
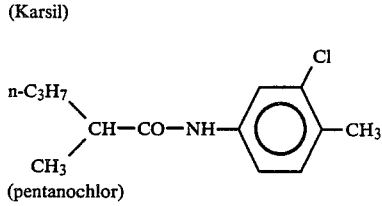
(pentanochlor) (I-E-4)
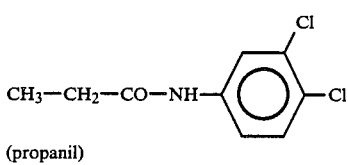
(propanil) (I-E-5)
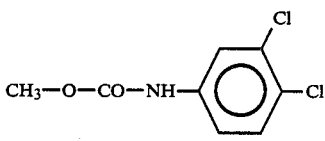
(swep) (I-E-6)
(F) uracil derivatives of the formulae
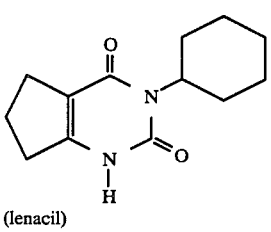
(lenacil) (I-F-1)
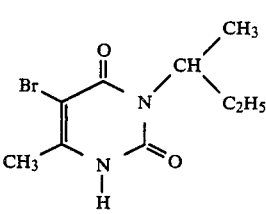
(I-F-2)

-continued

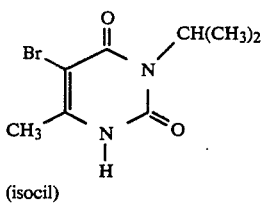
(bromacil)

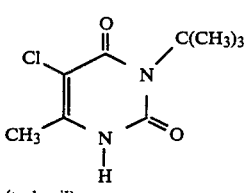
(isocil)

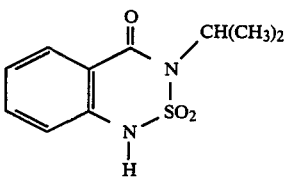
(terbacil)

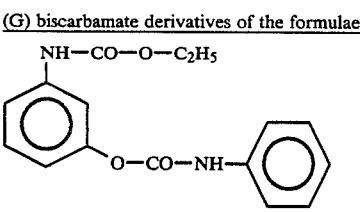
(bentazon)

(G) biscarbamate derivatives of the formulae

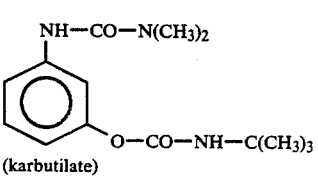
(desmedipham)

(I-G-1)

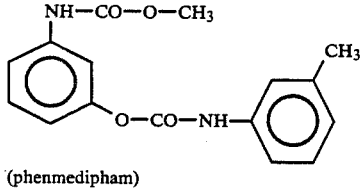
(karbutilate)

(I-G-2)

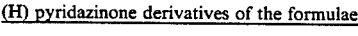
(phenmedipham)

(I-G-3)

(H) pyridazinone derivatives of the formulae

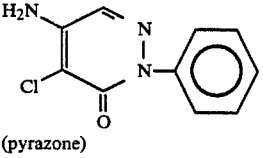
(pyrazone)

(I-H-1)

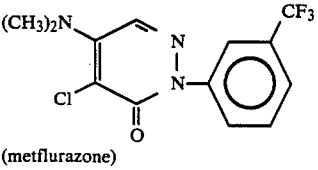
(metflurazone)

(I-H-2)

-continued

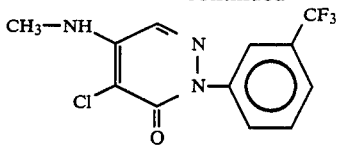
(norflurazon)

(I-H-3)

(J) hydroxybenzonitrile derivatives of the formulae

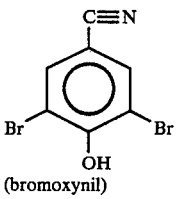
(bromoxynil)

(I-J-1)

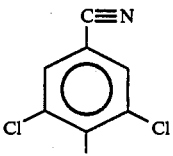
(chloroxynil)

(I-J-2)

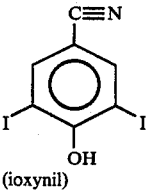
(ioxynil)

(I-J-3)

The photosynthesis-inhibiting active compounds of the formulae (I-A to I-J) are known (compare, for example, Carl Fedtke, Biochemistry and Physiology of Herbicide Action, Springer-Verlag, 1982).

Formula (II) provides a general definition of the carbamate derivatives also to be used as components in the mixture. Preferably, in this formula, $R^1$ represents straight-chain or branched alkyl with 1 to 8 carbon atoms, halogenoalkyl with 1 or 2 carbon atoms and 1 to 5 halogen atoms (such as, in particular, fluorine and chlorine atoms), alkenyl or alkinyl with in each case 3 to 6 carbon atoms or phenyl;

$R^2$ represents straight-chain or branched alkyl with 1 to 8 carbon atoms, halogenoalkyl with 1 to 5 carbon atoms and 1 to 3 halogen atoms (such as, in particular, fluorine and chlorine atoms), alkoxy with 1 to 4 carbon atoms, or cycloalkyl or cycloalkylalkyl with in each case 3 to 6 carbon atoms in the alkyl part and in each case optionally substituted by alkyl with 1 to 4 carbon atoms;

$R^3$ represents hydrogen or the grouping $-CO-OR^4$, $-CO-CO-OR^5$ or $-CO-CO-NR^6R^7$;

$R^4$ represents straight-chain or branched alkyl with 1 to 4 carbon atoms, alkenyl or alkinyl with in each case 3 to 4 carbon atoms, or phenyl which is optionally substituted by halogen and/or alkyl with 1 or 2 carbon atoms;

$R^5$ represents straight-chain or branched alkyl with 1 to 4 carbon atoms, or alkenyl or alkinyl with in each case 3 or 4 carbon atoms; and $R^6$ and $R^7$, which are identical or different, represent hydrogen, straight-chain or branched alkyl with 1 to 6 carbon atoms or alkenyl with 3 to 4 carbon atoms.

Particularly preferred compounds of the formula (II) are those in which $R^1$ represents straight-chain or branched alkyl with 1 to 5 carbon atoms, such as, in particular, methyl; or furthermore represents chloroethyl, fluoroethyl, trifluoroethyl or trichloroethyl; or represents alkyl, propargyl, 3-butin-2-yl or phenyl;

$R^2$ represents straight-chain or branched alkyl with 1 to 8 carbon atoms; or represents chloroethyl, fluoroethyl, trifluoroethyl or trichloroethyl, or tert.-butyl or neopentyl, each of which is mono-, di- or tri-substituted by fluorine or chlorine; or furthermore represents cyclopropyl, cyclopropylmethyl, cyclopentyl, cyclopentylmethyl cyclohexyl or cyclohexylmethyl, each of which is optionally substituted by methyl; or represents alkoxy with 1 to 4 carbon atoms, allyl or propargyl;

$R^3$ represents hydrogen or the grouping —CO—OR$^4$, —CO—CO—OR$^5$ or —CO—CO—NR$^6$R$^7$;

$R^4$ represents methyl, allyl, propargyl or phenyl;

$R^5$ represents straight-chain or branched alkyl with 1 to 4 carbon atoms, such as, in particular, methyl; or represents allyl or propargyl; and $R^6$ and $R^7$ are identical or different and represent hydrogen, straight-chain or branched alkyl with 1 to 5 carbon atoms, allyl or propargyl.

The carbamate derivates of the formula (IL) are known (compare, for example, German Offenlegungsschriften [German Published Specification] Nos. 3,035,392, 3,035,393, 3,230,294 and 3,230,295; or they are the subject of commonly assigned pending applications (compare German Patent Application Nos. P 33 12 498 of Apr. 7, 1983 and P 33 26 145 of July 20, 1983; or they can be obtained in the customary manner by processes described in these references, for example by reacting amines, if appropriate in the form of their hydrosalts, with carbonic acid ester-halides; or by reacting isocyanates with alcohols in the presence of a catalyst; or by reacting chlorooxalylcarbamic acid esters with alcohols or amines (in this context, compare also the preparation examples).

The weight ratios of the active compounds in the new active compound combinations can vary within relatively wide limits. In general, 0.25 to 100, preferably 5 to 50 and in particular 10 to 20, parts by weight of carbamate derivative of the formula (II) (synergist) are present per part by weight of photosynthesis-inhibiting active compound (herbicidal active compound).

The photosynthesis-inhibiting active compounds exhibit powerful herbicidal actions. Nevertheless, against some broad-leaved weeds, such as, for example, *Galium aparine, Ipomoea hederacea, Datura stramonium, Cirsium arvense, Convolvulus arvensis* or *Solanum nigrum*, and some gramineous weeds, such as, for example, *Agropyron repens, Avena fatua, Cynodon dactylon, Cyperus ssp.* and *Lolium rigidum,* they have an action which is not always adequate. The active compound combinations according to the invention extend the action spectrum of the compounds of the formulae (I-A to 1-J) and thereby enable these weeds which can be controlled only with difficulty or not at all by the herbicidal active compounds by themselves to be combated.

The active compound combinations according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Vicia, Nicotiana, Lycopersicon, Arachis, Brassica, Lactuca, Cucumis and Cucurbita.

Monocotyledon weeds of the genera: Echinochloa, Setaria, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrotis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

Besides a good action against graminaceous weeds, the active compound combinations according to the invention also exhibit a good herbicidal action on broad-leaved weeds.

The active compound combinations according to the invention can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main; aromatics, such as xylene, toluene or alkyl napthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

The formulations can contain, as further additives, colorants such as inorganic pigments, for example iron oxide, titanium oxide and Prussian Blue, and organic dyestuffs, such as alizarin dyestuffs, azo dyestuffs and metal phthalocyanine dyestuffs, and moreover trace nutrients such as salts of iron, manganese, boron, copper, cobalt, molybdenum and zinc.

The formulations in general contain between 0.1 and 95 percent by weight of active compound combination, preferably between 0.5 and 90%.

The active compound combinations according to the invention are in general used in the form of finished formulations. However, the active compounds contained in the active compound combinations can also be mixed as individual formulations when used, that is to say can be applied in the form of tank mixes.

The new active compound combinations, as such or in the form of their formulations, can furthermore also be used as mixtures with other known herbicides, finished formulations or tank mixes again being possible. Mixtures with other known active compounds, such as fungicides, insecticides, acaricides, nematicides, bird repellents, growth factors, plant nutrients and agents which improve soil structure, are also possible.

The new active compound combinations can be used as such, in the form of their formulations or in the use forms prepared therefrom by further dilutions, such as ready-to-use solutions, suspensions, emulsions, powders, pastes and granules. They are used in the customary manner, for example by watering, spraying, atomizing, dusting or scattering.

The active compound combinations according to the invention can be applied either before or after sowing as well as after emergence of the plants, together or in separate applications. The sequence of applications is of no importance here.

When the synergists according to the invention are used, the customary application amount of the herbicides of the formulae (I-A to I-J) can be reduced. The amount of herbicidal photosynthesis-inhibiting active compound applied in the case of surface treatment is between 0.01 and 3.0 kg/ha, preferably between 0.05 and 2.0 kg/ha.

The amount of synergistic carbamate derivative (II) applied in the case of surface treatment is between 0.1 and 10 kg/ha, preferably between 0.05 and 3 kg/ha.

The good herbicidal action of the active compound combinations according to the invention can be seen from the following examples. While the individual active compounds show weaknesses in herbicidal action, the combinations according to the invention exhibit a herbicidal action which goes beyond a simple summation of the actions.

A synergistic effect is always present with herbicides if the herbicidal action of the active compound combination is greater than the sum of the actions of the active compounds applied.

EXAMPLE A

Pre-emergence test

Solvent: 5 parts by weight of acetone

Emulsifier: 1 part by weight of alkylaryl polyglycol ether

To produce a suitable preparation of active compound, 1 part by weight of herbicidal active compound or synergist or of a mixture of herbicidal active compound and synergist is mixed with the stated amount of solvent, the stated amount of emulsifier is added and the concentrate is diluted with water to the desired concentration.

Seeds of the test plants are sown in normal soil and, after 24 hours, watered with a herbicide preparation or with the synergist preparation or with the preparation of synergist and herbicidally active compound. It is expedient to keep constant the amount of water per unit urea. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

The active compounds, amount applied and results can be seen from the following tables.

Table $A_1$/pre-emergence test

Synergistic action of carbamate derivatives (II) (=synergist S) and 4-amino-6-tert.-butyl-3-methyl-thio-1,2,4-triazin-5-one (I-A-1) (=herbicide H) on Ipomoea hederacea. The amount applied in kg/ha relates to the content of active compound.

TABLE $A_1$

| Structure of the synergist (II) | S (kg/ha) | H (kg/ha) | % activity on *Ipomoea hederacea* | | |
|---|---|---|---|---|---|
| | | | H | S | H + S |
| CH$_2$F<br>\|<br>CH$_2$F—C—NH—CO—O—CH$_2$—C≡CH<br>\|<br>CH$_2$F  (II-11) | 0.5<br>2<br>0.5<br>2 | 0.05<br>0.05<br>0.15<br>0.15 | 10<br>10<br>30<br>30 | 0<br>0<br>0<br>0 | 50<br>90<br>100<br>100 |
| CH$_2$Cl<br>\|<br>CH$_2$Cl—C—NH—CO—O—CH$_2$—C≡CH<br>\|<br>CH$_2$Cl  (II-24) | 0.03<br>0.1<br>0.3<br>1<br>2 | 0.1<br>0.1<br>0.1<br>0.1<br>0.1 | 30<br>30<br>30<br>30<br>30 | 10 | 100<br>90<br>100<br>100<br>100 |

TABLE A₁-continued

| Structure of the synergist (II) | S (kg/ha) | H (kg/ha) | % activity on *Ipomoea hederacea* H | S | H + S |
|---|---|---|---|---|---|
| CH₂F−C(CH₂F)(CH₂F)−CH₂−NH−CO−O−CH₂−C≡CH (II-1) | 0.03 | 0.1 | 0 | 0 | 70 |
|  | 0.1 | 0.1 | 0 |  | 100 |
|  | 0.3 | 0.1 | 0 |  | 80 |
|  | 1 | 0.1 | 0 |  | 90 |
|  | 2 | 0.1 | 0 |  | 90 |
| CH₃−C(CH₂F)(CH₂F)−CH₂−NH−CO−O−C≡CH (II-25) | 0.03 | 0.1 | 10 | 0 | 90 |
|  | 0.1 | 0.1 | 10 |  | 90 |
|  | 0.3 | 0.1 | 10 |  | 100 |
|  | 1 | 0.1 | 10 |  | 100 |
|  | 2 | 0.1 | 10 |  | 100 |
| CH₂F−C(CH₃)(CH₃)−CH₂−NH−CO−O−CH₂−C≡CH (II-12) | 0.03 | 0.1 | 0 | 0 | 20 |
|  | 0.1 | 0.1 | 0 |  | 20 |
|  | 0.3 | 0.1 | 0 |  | 50 |
|  | 1 | 0.1 | 0 |  | 90 |
|  | 2 | 0.1 | 0 |  | 90 |
| CH₃−C(CH₂Cl)(CH₂Cl)−NH−CO−O−CH₂−C≡CH (II-26) | 0.03 | 0.1 | 20 | 10 | 90 |
|  | 0.1 | 0.1 | 20 |  | 100 |
|  | 0.3 | 0.1 | 20 |  | 90 |
|  | 1 | 0.1 | 20 |  | 100 |
|  | 2 | 0.1 | 20 |  | 100 |
| CH₂Cl−C(CH₃)(CH₃)−NH−CO−O−CH₂−C≡CH (II-27) | 0.03 | 0.1 | 20 | 10 | 90 |
|  | 0.1 | 0.1 | 20 |  | 100 |
|  | 0.3 | 0.1 | 20 |  | 100 |
|  | 1 | 0.1 | 20 |  | 100 |
|  | 2 | 0.1 | 20 |  | 100 |
| CH₂F−C(CH₂F)(CH₃)−NH−CO−O−CH₂−C≡CH (II-2) | 0.03 | 0.1 | 10 | 10 | 40 |
|  | 0.1 | 0.1 | 10 |  | 50 |
|  | 0.3 | 0.1 | 10 |  | 50 |
|  | 1 | 0.1 | 10 |  | 90 |
|  | 2 | 0.1 | 10 |  | 100 |
| CH₃−C(CH₂F)(CH₃)−NH−CO−O−CH₂−C≡CH (II-13) | 0.03 | 0.1 | 10 | 10 | 20 |
|  | 0.1 | 0.1 | 10 |  | 50 |
|  | 0.3 | 0.1 | 10 |  | 90 |
|  | 1 | 0.1 | 10 |  | 90 |
|  | 2 | 0.1 | 10 |  | 100 |
| CH₂Cl−C(CH₃)(CH₃)−CH₂−NH−COO−CH₂−C≡CH (II-14) | 0.03 | 0.1 | 0 | 0 | 50 |
|  | 0.1 | 0.1 | 0 |  | 30 |
|  | 0.3 | 0.1 | 0 |  | 40 |
|  | 1 | 0.1 | 0 |  | 90 |
|  | 2 | 0.1 | 0 |  | 90 |
| CH₃−C(CH₂Cl)(CH₂Cl)−NH−COOCH₃ (II-15) | 0.03 | 0.1 | 0 | 0 | 10 |
|  | 0.1 | 0.1 | 0 |  | 20 |
|  | 0.3 | 0.1 | 0 |  | 20 |
|  | 1 | 0.1 | 0 |  | 40 |
|  | 2 | 0.1 | 0 |  | 70 |
| CH₃−C(CH₂Cl)(CH₂Cl)−NH−CO−O−CH₂−CH=CH₂ (II-17) | 0.03 | 0.1 | 0 | 0 | 20 |
|  | 0.1 | 0.1 | 0 |  | 20 |
|  | 0.3 | 0.1 | 0 |  | 20 |
|  | 1 | 0.1 | 0 |  | 50 |
|  | 2 | 0.1 | 0 |  | 90 |
| (CH₃)₃C−O−NH−CO−O−C₆H₅ (II-6) | 0.5 | 0.05 | 0 | 0 | 0 |
|  | 2 | 0.05 | 10 | 0 | 100 |
|  | 0.5 | 0.15 | 0 | 0 | 0 |
|  | 2 | 0.15 | 10 |  | 100 |
| cyclopropyl−NH−CO−O−C₆H₅ (II-7) | 0.5 | 0.05 | 0 | 0 | 100 |
|  | 2 | 0.05 | 0 |  | 80 |
|  | 0.5 | 0.15 | 10 |  | 100 |
|  | 2 | 0.15 | 10 |  | 100 |
| cyclopropyl−N(CO−O−C₆H₅)₂ (II-10) | 0.5 | 0.05 | 0 | 0 | 50 |
|  | 2 | 0.05 | 0 |  | 40 |
|  | 0.5 | 0.15 | 10 |  | 100 |
|  | 2 | 0.15 | 10 |  | 100 |

TABLE A₁-continued

| Structure of the synergist (II) | S (kg/ha) | H (kg/ha) | % activity on *Ipomoea hederacea* H | S | H + S |
|---|---|---|---|---|---|
| Cl—CH₂—CH₂—N(CO—O—C₆H₅)₂ (II-42) | 0.5 | 0.05 | 0 | 0 | 10 |
| | 2 | 0.05 | 0 | 0 | 20 |
| | 0.5 | 0.15 | 10 | 0 | 20 |
| | 2 | 0.15 | 10 | 0 | 50 |
| Cl—CH₂—CH₂—NH—CO—O—C₆H₅ (II-8) | 0.5 | 0.05 | 0 | 0 | 10 |
| | 2 | 0.05 | 0 | 10 | 30 |
| | 0.5 | 0.15 | 10 | 0 | 30 |
| | 2 | 0.15 | 10 | 10 | 100 |
| cyclopropyl-CH₂—NH—CO—O—C₆H₅ (II-43) | 0.5 | 0.05 | 0 | 0 | 20 |
| | 2 | 0.05 | 0 | 0 | 70 |
| | 0.5 | 0.15 | 10 | 0 | 50 |
| | 2 | 0.15 | 10 | 0 | 80 |
| cyclopropyl-C(CH₃)(NH—CO—O—C₆H₅) (II-9) | 0.03 | 0.1 | 20 | 0 | 10 |
| | 0.1 | 0.1 | 20 | | 10 |
| | 0.3 | 0.1 | 20 | | 90 |
| | 1 | 0.1 | 20 | | 90 |
| | 2 | 0.1 | 20 | | 50 |
| (CH₃)₃C—CH₂—N(COOCH₃)(COO—CH₂—C≡CH) (II-56) | 0.5 | 0.05 | 10 | 0 | 80 |
| | 2 | 0.05 | 10 | 0 | 100 |
| | 0.5 | 0.15 | 30 | 0 | 100 |
| | 2 | 0.15 | 30 | 0 | 100 |
| (CH₃)₃C—CH(CH₃)—NH—CO—O—CH₂—C≡CH (II-57) | 0.03 | 0.1 | 0 | 10 | 40 |
| | 0.1 | 0.1 | 0 | | 90 |
| | 0.3 | 0.1 | 0 | | 90 |
| | 1 | 0.1 | 0 | | 90 |
| | 2 | 0.1 | 0 | | 100 |
| tC₄H₉—CH₂—N(COOCH₂—C≡CH)(CO—COO—CH₂—C≡CH) (II-59) | 0.5 | 0.05 | 0 | 0 | 30 |
| | 2 | 0.05 | 0 | 0 | 70 |
| | 0.5 | 0.15 | 10 | 0 | 90 |
| | 2 | 0.15 | 10 | 0 | 100 |
| cyclohexyl-CH₂—NH—COO—CH₂—C≡CH (II-60) | 0.03 | 0.1 | 10 | 10 | 10 |
| | 0.1 | 0.1 | 10 | | 10 |
| | 0.3 | 0.1 | 10 | | 20 |
| | 1 | 0.1 | 10 | | 50 |
| | 2 | 0.1 | 10 | | 90 |
| (CH₃)₃C—CH₂—NH—COO—CH₂—C≡CH (II-3) | 0.5 | 0.05 | 10 | 0 | 60 |
| | 2 | 0.05 | 10 | 0 | 70 |
| | 0.5 | 0.15 | 20 | 0 | 100 |
| | 2 | 0.15 | 20 | 0 | 100 |
| cyclopentyl-N—(COO—CH₂—C≡CH)₂ (II-62) | 0.5 | 0.05 | 0 | 0 | 20 |
| | 2 | 0.05 | 0 | 0 | 30 |
| | 0.5 | 0.15 | 0 | 0 | 70 |
| | 2 | 0.15 | 0 | 0 | 100 |
| (C₂H₅)₂CH—NH—COO—CH₂—C≡CH (II-63) | 0.5 | 0.05 | 0 | 0 | 50 |
| | 2 | 0.05 | 0 | 0 | 80 |
| | 0.5 | 0.15 | 0 | 0 | 100 |
| | 2 | 0.15 | 0 | 0 | 100 |
| (CH₃)₃C—NH—COO—CH₂—C≡CH (II-64) | 0.03 | 0.1 | 10 | 0 | 40 |
| | 0.1 | 0.1 | 10 | | 50 |
| | 0.3 | 0.1 | 10 | | 90 |
| | 1 | 0.1 | 10 | | 90 |
| | 2 | 0.1 | 10 | | 100 |

TABLE A1-continued

| Structure of the synergist (II) | S (kg/ha) | H (kg/ha) | % activity on *Ipomoea hederacea* | | |
|---|---|---|---|---|---|
| | | | H | S | H + S |
| tC$_4$H$_9$—CH$_2$—NH—COO—CH(CH$_3$)—C≡CH (II-65) | 0.5 | 0.05 | 0 | 0 | 80 |
| | 2 | 0.05 | 0 | 0 | 100 |
| | 0.5 | 0.15 | 20 | 0 | 100 |
| | 2 | 0.15 | 20 | 0 | 100 |
| tC$_4$H$_9$—CH(CH$_3$)—NH—COO—CH$_2$—CF$_3$ (II-66) | 0.5 | 0.05 | 0 | 0 | 30 |
| | 2 | 0.05 | 0 | 0 | 90 |
| | 0.5 | 0.15 | 10 | 0 | 60 |
| | 2 | 0.15 | 10 | 0 | 100 |
| tC$_4$H$_9$—CH$_2$—NH—COO—CH$_2$—CF$_3$ (II-67) | 0.5 | 0.05 | 0 | 0 | 40 |
| | 2 | 0.05 | 0 | 0 | 50 |
| | 0.5 | 0.15 | 0 | 0 | 50 |
| | 2 | 0.15 | 0 | 0 | 60 |
| tC$_4$H$_9$—CH$_2$—NH—COO—CH$_2$—CH=CH$_2$ (II-68) | 0.5 | 0.05 | 0 | 0 | 20 |
| | 2 | 0.05 | 0 | 0 | 90 |
| | 0.5 | 0.15 | 10 | 0 | 80 |
| | 2 | 0.15 | 10 | 0 | 100 |
| tC$_4$H$_9$—CH$_2$—N(COO—CH$_2$—C≡CH)(CO—CO—NH—C$_4$H$_9$n) (II-69) | 0.5 | 0.05 | 10 | 0 | 20 |
| | 2 | 0.05 | 10 | 0 | 20 |
| | 0.5 | 0.15 | 30 | 0 | 30 |
| | 2 | 0.15 | 30 | 0 | 90 |
| tC$_4$H$_9$—CH$_2$—N(COO—CH$_2$—C≡CH)(CO—CO—N(CH$_2$—CH=CH$_2$)$_2$) (II-4) | 0.5 | 0.05 | 0 | 0 | 20 |
| | 2 | 0.05 | 0 | 0 | 50 |
| | 0.5 | 0.15 | 10 | 0 | 100 |
| | 2 | 0.15 | 10 | 0 | 50 |
| tC$_4$H$_9$—CH$_2$—N(COO—CH$_2$—C≡CH)(CO—CO—NH—CH$_2$—CH=CH$_2$) (II-70) | 0.5 | 0.05 | 0 | 10 | 60 |
| | 2 | 0.05 | 0 | 10 | 80 |
| | 0.5 | 0.15 | 10 | 10 | 100 |
| | 2 | 0.15 | 10 | 10 | 100 |
| tC$_4$H$_9$—CH$_2$—N(COO—CH$_2$—C≡CH)(CO—CO—N(C$_4$H$_9$n)$_2$) (II-71) | 0.5 | 0.05 | 0 | 0 | 20 |
| | 2 | 0.05 | 0 | 0 | 30 |
| | 0.5 | 0.15 | 10 | 0 | 40 |
| | 2 | 0.15 | 10 | 0 | 70 |
| tC$_4$H$_9$—CH$_2$—N(COO—CH$_2$—C≡CH)(CO—CO—N(CH$_3$)$_2$) (II-72) | 0.5 | 0.05 | 0 | 0 | 40 |
| | 2 | 0.05 | 0 | 0 | 90 |
| | 0.5 | 0.15 | 10 | 0 | 100 |
| | 2 | 0.15 | 10 | 0 | 100 |
| tC$_4$H$_9$—CH$_2$—N(COO—CH$_2$—C≡CH)(CO—CO—O—CH$_3$) (II-5) | 0.5 | 0.05 | 0 | 0 | 50 |
| | 2 | 0.05 | 0 | 0 | 60 |
| | 0.5 | 0.15 | 0 | 0 | 80 |
| | 2 | 0.15 | 0 | 0 | 90 |
| tC$_4$H$_9$—CH$_2$—N(COO—CH$_2$—C≡CH)(CO—CO—O—CH$_2$—CH=CH$_2$) (II-73) | 0.5 | 0.05 | 0 | 0 | 80 |
| | 2 | 0.05 | 0 | 0 | 80 |
| | 0.5 | 0.15 | 10 | 0 | 90 |
| | 2 | 0.15 | 10 | 0 | 100 |

TABLE A1-continued

| Structure of the synergist (II) | S (kg/ha) | H (kg/ha) | % activity on *Ipomoea hederacea* H | S | H + S |
|---|---|---|---|---|---|
| CH₃—C(CH₂F)(CH₂F)—NH—CO—CH₂—CH=CH₂ (II-18) | 0.03 | 0.1 | 10 | 0 | 30 |
|  | 0.1 | 0.1 | 10 |  | 40 |
|  | 0.3 | 0.1 | 10 |  | 40 |
|  | 1 | 0.1 | 10 |  | 90 |
|  | 2 | 0.1 | 10 |  | 90 |
| CH₃—C(CH₂Cl)(CH₂Cl)—NH—CO—O—CH₂—CH₂—Cl (II-22) | 0.03 | 0.1 | 10 | 0 | 20 |
|  | 0.1 | 0.1 | 10 |  | 20 |
|  | 0.3 | 0.1 | 10 |  | 40 |
|  | 1 | 0.1 | 10 |  | 70 |
|  | 2 | 0.1 | 10 |  | 100 |
| CH₂=CH—CH₂—N—(COO—C₆H₅)₂ (II-36) | 0.03 | 0.1 | 0 | 0 | 20 |
|  | 0.1 | 0.1 | 0 |  | 40 |
|  | 0.3 | 0.1 | 0 |  | 40 |
|  | 1 | 0.1 | 0 |  | 80 |
|  | 2 | 0.1 | 0 |  | 80 |

Use of the herbicide (I-A-1) by itself in a concentration of 0.5 or 2.0 kg/ha leads to 80 and, respectively, 95% damage on *Ipomoea hederacea*.

Table A₂

Synergistic activity of the carbamate derivative according to preparation Example (II-26) and various photosynthesis-inhibiting herbicides on *Ipomoea hederacea*.

Synergist: preparation Example (II-26)
Mixing ratio herbicide (H): synergist (S)=1:4
Test plants: *Ipomoea hederacea*

| Treatment | Herbicide without synergist % activity (kg/ha of H) | Herbicide + synergist % activity (kg/ha of H + S) |
|---|---|---|
| metribuzin (I-A-1) ± (II-26) | 3 (0.1) | 100 (0.1 + 0.4) |
| ametridione (I-B-1) ± (II-26) | 1 (0.2) | 95 (0.2 + 0.8) |
| atrazine (I-C-1) ± (II-26) | 16 (0.025) | 45 (0.025 + 0.1) |
| linuron (I-D-1) ± (II-26) | 14 (0.1) | 98 (0.1 + 0.4) |
| —(II-26) | — | 15 (0 + 0.8) |

PREPARATION EXAMPLES

Example 1

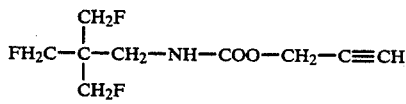

16.7 g of 2,2-bisfluoromethyl-3-fluoropropyl isocyanate (29% strength solution in toluene) are dissolved in 100 ml of toluene, and 10 mg of diazabicyclooctane (Dabco) are added. 5.6 g of 2-propinyl alcohol are added dropwise to this reaction mixture at room temperature (about 20° C.). After the reaction mixture has been heated at the boiling point for four hours, it is cooled and washed with water. After drying over sodium sulphate, the solvent is distilled off and the oil which remains is freed from residual solvent under a high vacuum. 22 g of O-2-propinyl N-(2,2-bisfluoromethyl-3-fluoro-propyl)-carbamate are obtained in the form of a colorless oil (yield of 80% of theory), $n_{66D}^{20}$: 1.4505.

Example 2

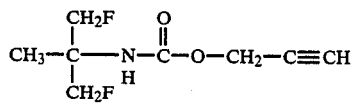

14 g (0.1 mole) of 2,2-bisfluoromethylpropanoylfluoride are dissolved in 200 ml of acetone. A solution of 6.5 g (0.1 mole) of sodium azide in 20 ml of water is added dropwise at 0° C., the mixture is stirred at room temperature for one hour and 200 ml of water are added. The aqueous phase is extracted twice with 200 ml of toluene each time and the resulting combined toluene phase is washed twice with 200 ml of water each time. After drying over sodium sulphate, the toluene phase is slowly heated to 70° to 80° C. until the evolution of gas which occurs has ended. The mixture is then boiled under reflux for one hour. Completion of the formation of the 1,1-bis-fluoromethylethylisocyanate is monitored by IR spectroscopy (decrease $\nu CON_3 = 2120$ cm$^{-1}$, increase $\nu N=C=O = 2250$ cm$^{-1}$). 11.2 g of 2-propinyl alcohol are added dropwise to the solution of the 1,1-bisfluoromethyl-ethylisocyanate obtained in this manner, 10 mg of diazabicyclooctane (Dabco) are added and the subsequent procedure is as under preparation Example 1. 13 g of O-2-propinyl N-(1,1-bisfluoromethyl-ethyl)-carbamate are obtained in the form of a colorless oil (yield of 68% of theory), $n_D^2$: 1.4430.

Example 3

(CH₃)₃C—CH₂—NH—CO—O—CH₂—C≡CH 4520 g (40 moles) of neopentylisocyanate and 1 g of diazabicyclooctane (Dabco) are heated to 80° C. (10 l flask) and 2240 g (40 moles) of propargyl alcohol are then added in the course of 1.5 hours. When the addition of the alcohol has ended, IR spectra are used to monitor whether the reaction is complete. When the NCO band has disappeared, the mixture is distilled under a high vacuum. 6395 g (95% of theory) of 2-propinyl N-neopentylcarbamate of boiling point: 85° C./40 mbar are obtained.

Example 4

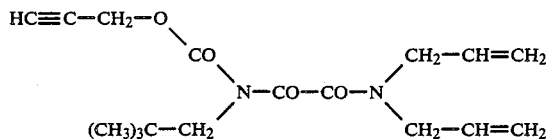

3.88 g (0.4 mole) of diallylamine are added dropwise to 5.35 g (0.02 mole) of 97% pure N-neopentyl-N-2-propinyloxycarbonyloxamic acid chloride in 50 ml of toluene. During this addition, the internal temperature is kept at 20° C. by external cooling with ice. When the dropwise addition has ended, 30 ml of water are added, the organic phase is separated off and the latter is washed twice with water, dried over sodium sulphate and finally concentrated in vacuo. 5.5 g (86% of theory) of N,N-diallyl-N'-neopentyl-N'-2-propinyloxycarbonyl-oxalic acid diamide of refractive index $n_D^{20} = 1.4878$ are obtained.

Example 5

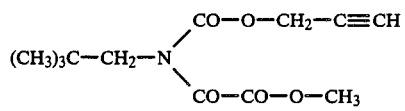

0.64 g (0.02 mole) of methanol are added to 5.35 g (0.02 mole) of 97% pure N-neopentyl-N-2-propinyloxycarbonyloxamic acid chloride in 50 ml of toluene, and 2.02 g (0.02 mole) of triethylamine are then added dropwise, while cooling with ice. After the precipitate has been filtered off, the filtrate is washed with water, dried over sodium sulphate and freed from the solvent under a high vacuum. 5 g (98% of theory) of methyl N-neopentyl-N-2-propinyloxycarbonyl-oxamate of refractive index $n_D^{20} = 1.4634$ are obtained.

Example 6

A solution of about 2 moles of O-tert.-butylhydroxylamine (obtained from 2 moles of O-tert.-butyl-phthaloxime+hydrazine hydrate in dioxane, after the phthalazine formed has been filtered off with suction) in 2.2 l of dioxane and a solution of 80 g (2 moles) of sodium hydroxide in 2.2 l of water are simultaneously added dropwise to a solution of 313 g (2 moles) of phenylchloroformate in 2 l of methylene chloride at 10° to 13° C. The mixture is subsequently stirred at room temperature for 4 hours, 2 l of water are added and the phases are separated. The organic phase is washed several times with water and dried at 80° C. in vacuo. 333 g (80% of theory) of O-phenyl N-tert.-butoxy-carbamate of melting point 124° to 126° C. are obtained.

Example 7

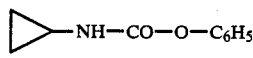

291 g=260 ml (5 moles) of 98% pure cyclopropylamine and 360 ml of sodium hydroxide solution containing 200 g (5 moles) of sodium hydroxide are simultaneously added dropwise to a solution of 782.5 g (5 moles) of phenylchloroformate in 2.5 l of methylene chloride at 15° to 20° C. The mixture is subsequently stirred for one hour, without cooling, 1 l of water is added and the organic phase is separated off and concentrated. 880 g of O-phenyl-N-cyclopropyl-carbamate of melting point 66° to 68° C. are obtained; purity according to gas chromatography: 98.5% (98% of theory).

Example 8

1500 ml of an aqueous solution of 696 g (6 moles) of 2-chloroethylamine hydrochloride and 1500 g of sodium hydroxide solution containing 480 g (12 moles) of sodium hydroxide are simultaneously added dropwise to a solution of 936 (6 moles) of phenylchloroformate in 3 l of methylene chloride at 15° to 20° C. The mixture is worked up as described under Example 7 to give 1161 g of O-phenyl N-(2-chloroethyl)-carbamate of melting point 65° to 67° C.; purity according to gas chromatography: 95.7% (93% of theory).

Example 9

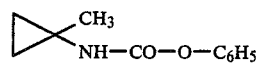

108.6 g (0.99 mole) of 1-methyl-cyclopropyl isocyanate (content according to gas chromatography: 88.5%), 93.1 g (0.99 mole) of phenol and 0.6 g of diazabicyclooctane (DABCO) are heated under reflux for 20 hours. 111.7 g of O-phenyl N-(1-methylcyclopropyl)-carbamate of melting point 118° to 119° C. crystallise out at room temperature; a further 13.9 g can be obtained from the concentrated filtrate (total yield: 66% of theory).

Example 10

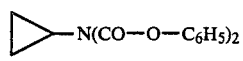

A solution of 593 g (3 moles) of O-phenyl N-cyclopropyl-carbamate in 500 ml of methylene chloride is uniformly added dropwise below the surface of 4695 g (30 moles) of boiling phenyl chloroformate at 184° to 191° C. in the course of 8 hours, a stream of nitrogen being passed through the sump and the solvent being distilled off through a reflux condenser kept at 100° C. The mixture is heated for a further hour, while passing further nitrogen through, the phenyl chloroformate excess is distilled off in vacuo and the residue is fractionated under a high vacuum. 2271 g of diphenyl N-cyclopropylimidodicarboxylate of boiling point 143° C./0.01 mbar are obtained; purity according to gas chromatography: 98.5% (84% of theory). The product solidifies; a sample recrystallized from a little methanol has a melting point of 90° to 92° C.

The carbamate derivatives of the general formula (II)

Listed in the following Table 1 can be obtained in an analogous manner:

TABLE 1

| Ex. No. | R$^1$ | R$^2$ | R$^3$ | Melting point (°C.) or boiling point (°C./mmHg) or n$_D^{20}$ |
|---|---|---|---|---|
| 11 | —CH$_2$—C≡CH | (FCH$_2$)$_3$C— | H | 1.4371 |
| 12 | —CH$_2$—C≡CH | FCH$_2$—C(CH$_3$)$_2$—CH$_2$— | H | 1.4580 |
| 13 | —CH$_2$—C≡CH | FCH$_2$—C(CH$_3$)$_2$— | H | 1.4470 |
| 14 | —CH$_2$—C≡CH | ClCH$_2$—C(CH$_3$)$_2$—CH$_2$— | H | 195/0.08 |
| 15 | —CH$_3$ | CH$_3$—C(CH$_2$Cl)$_2$— | H | 42–44 |
| 16 | —CH$_2$—C(CH$_3$)$_3$ | CH$_3$—C(CH$_2$Cl)$_2$— | H | 41–43 |
| 17 | —CH$_2$—CH=CH$_2$ | CH$_3$—C(CH$_2$Cl)$_2$— | H | 1.4851 |
| 18 | —CH$_2$—CH=CH$_2$ | CH$_3$—C(CH$_2$F)$_2$— | H | 1.4320 |
| 19 | —C$_3$H$_7$—n | CH$_3$—C(CH$_2$Cl)$_2$— | H | 130/0.5 |
| 20 | —C$_3$H$_7$—i | CH$_3$—C(CH$_2$Cl)$_2$— | H | 140/0.5 |
| 21 | —C$_2$H$_5$ | CH$_3$—C(CH$_2$Cl)$_2$— | H | 135/0.5 |
| 22 | —CH$_2$CH$_2$Cl | CH$_3$—C(CH$_2$Cl)$_2$— | H | 1.4950 |
| 23 | —CH$_2$CCl$_3$ | CH$_3$—C(CH$_2$Cl)$_2$— | H | 180/0.06 |
| 24 | —CH$_2$—C≡CH | (ClCH$_2$)$_3$C— | H | 55 |
| 25 | —CH$_2$—C≡CH | CH$_3$—C(CH$_2$F)$_2$—CH$_2$— | H | 1.4505 |
| 26 | —CH$_2$—C≡CH | CH$_3$—C(CH$_2$Cl)$_2$— | H | 1.4952 |
| 27 | —CH$_2$—C≡CH | ClCH$_2$—C(CH$_3$)$_2$— | H | 1.4757 |
| 28 | 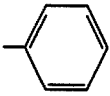 | (CH$_3$)$_3$C— | —CO—O—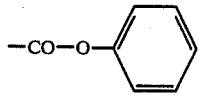 | 132 |
| 29 | 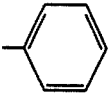 | CF$_3$—CH$_2$— | H | 88–90 |
| 30 | 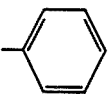 | CF$_3$—CH$_2$— | —CO—O—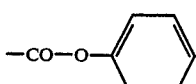 | 74–76 |
| 31 | 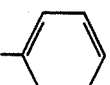 | (C$_2$H$_5$)$_2$CH— | —CO—O—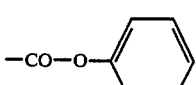 | 54–56 |
| 32 | 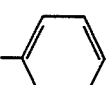 | (i-C$_3$H$_7$)$_2$CH— | H | 102–05 |
| 33 | 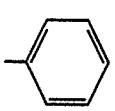 | $\begin{array}{c}\text{C}_2\text{H}_5\\\text{CH—CH}_2\text{—}\\\text{C}_4\text{H}_9\end{array}$ | —CO—O—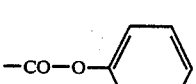 | 182–85/0.06 |
| 34 | 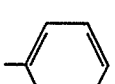 | (CH$_3$)$_3$C—CH(CH$_3$)— | —CO—O—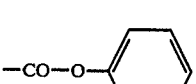 | 40–42 |
| 35 | 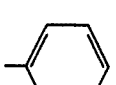 | CH$_3$—CF$_2$—CH$_2$— | —CO—O—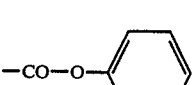 | 60–62 |
| 36 | 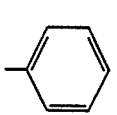 | CH$_2$=CH—CH$_2$— | —CO—O—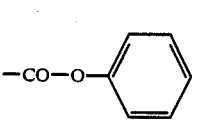 | 153/0.04 |

TABLE 1-continued
| Ex. No. | R¹ | R² | R³ | Melting point (°C.) or boiling point (°C./mmHg) or $n_D^{20}$ |
|---|---|---|---|---|
| 37 | Ph— | C₂H₅—C(CH₃)₂—CH₂— | —CO—O—Ph | 49–50 |
| 38 | —C₄H₉ | (CH₃)₃C—CH₂— | H | 118–20/18 |
| 39 | Ph— | (CH₃)₃C—CH₂CH₂— | —CO—O—Ph | 47–48 |
| 40 | Ph— | C₄H₉— | —CO—O—Ph | 165/0.4 |
| 41 | Ph— | 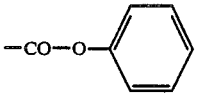 | —CO—O—Ph | 65–67 |
| 42 | Ph— | ClCH₂CH₂— | —CO—O—Ph | 66–68 |
| 43 | Ph— | 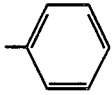—CH₂— | H | 59–61 |
| 44 | Ph— | C₂H₅O— | H | 41–43 |
| 45 | Ph— | i-C₃H₇O— | H | 48–51 |
| 46 | Ph— | C₂H₅\CH—CH₂— / CH₃ | —CO—O—Ph | 153–54/0.005 |
| 47 | Ph— | FCH₂—C(CH₃)₂—CH₂— | H | 61–63 |
| 48 | Ph— | CH₃—C(CH₂F)₂—CH₂— | H | 66–67 |
| 49 | Ph— | (FCH₂)₃C—CH₂— | H | 62–64 |
| 50 | Ph— | FCH₂—C(CH₃)—CH₂— | —CO—O—Ph | 74–76 |

TABLE 1-continued

| Ex. No. | R¹ | R² | R³ | Melting point (°C.) or boiling point (°C./mmHg) or $n_D^{20}$ |
|---|---|---|---|---|
| 51 | 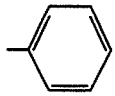 | $CH_3$—$(CH_2F)_2C$—$CH_2$— | —CO—O—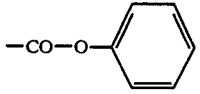 | 85–86 |
| 52 | 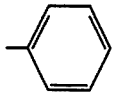 | $(FCH_2)_3C$—$CH_2$— | —CO—O—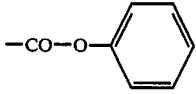 | 91–92 |
| 53 | 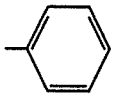 | 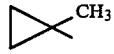 | —CO—O—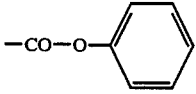 | 109–10 |
| 54 | 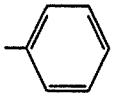 | $ClCH_2$—$C(CH_3)_2$—$CH_2$ | H | 68–69 |
| 55 | 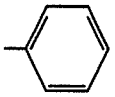 | $CH_3$—$C(CH_2Cl)_2$—$CH$— | H | 84–86 |
| 56 | —$CH_2$—C≡CH | $(CH_3)_3C$—$CH_2$— | —CO—O—$CH_3$ | |
| 57 | —$CH_2$—CH≡CH | $(CH_3)_3C$—$CH(CH_3)$— | H | 1.4642 |
| 58 | —$CH_2$—C≡CH | $(CH_3)_3C$—$CH_2$— | —CO—CO—$OC_4H_9$ | 1.4614 |
| 59 | —$CH_2$—C≡CH | $(CH_3)_3C$—$CH_2$— | —CO—CO—O—$CH_2$—C≡CH | 1.4738 |
| 60 | —$CH_2$—C≡CH | 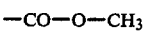—$CH_2$— | H | 125/0.06 |
| 61 | 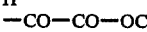 | $(CH_3)_3C$—$CH_2$— | —CO—CO—NH—$CH_2$—$C(CH_3)_3$ | 141–42 |
| 62 | —$CH_2$—C≡CH |  | —CO—O—$CH_2$—C≡CH | 1.4965 |
| 63 | —$CH_2$—C≡CH | $(C_2H_5)_2CH$— | H | 1.4572 |
| 64 | —$CH_2$—C≡CH | $(CH_3)_3C$— | H | 1.4498 |
| 65 | —$CH(CH_3)$—C≡CH | $(CH_3)_3C$—$CH_2$— | H | viscous oil |
| 66 | —$CH_2$—$CF_3$ | $(CH_3)_3C$—$CH(CH_3)$— | H | 43/0.04 |
| 67 | —$CH_2$—$CF_3$ | $(CH_3)_3C$—$CH_2$— | H | 38–40 |
| 68 | —$CH_2$—CH=$CH_2$ | $(CH_3)_3C$—$CH_2$— | H | 55/0.06 |
| 69 | —$CH_2$—C≡CH | $(CH_3)_3C$—$CH_2$— | —CO—CO—NH—$C_4H_9$ | 1.4753 |
| 70 | —$CH_2$—C≡CH | $(CH_3)_3C$—$CH_2$— | —CO—CO—NH—$CH_2$—CH=$CH_2$ | 1.4863 |
| 71 | —$CH_2$—C≡CH | $(CH_3)_3C$—$CH_2$— | —CO—CO—$N(C_4H_9)_2$ | 1.4739 |
| 72 | —$CH_2$—C≡CH | $(CH_3)_3C$—$CH_2$— | —CO—CO—$N(CH_3)_2$ | 1.4808 |
| 73 | —$CH_2$—C≡CH | $(CH_3)_3C$—$CH_2$— | —CO—CO—O—$CH_2$—CH=$CH_2$ | 1.4687 |

Another advantage of the invention is that it permits the weed-killing activity of the herbicide to be raised without increasing the amount of herbicide to a level at which it would damage a desired drop, such as cereals and especially soy beans, wheat, barley, oats, etc. Stated otherwise, the compositions can be highly selective.

It will be understood that the specification and examples are illustrative but not limitative of the present invention and that other embodiments within the spirit and scope of the invention will suggest themselves to those skilled in art.

What is claimed is:

1. In the combating of weeds in the growing of a cereal or soy beans by applying to the cereal, soy beans or to the field in which they are growing or are to be grown an amount of metribuzin effective to combat the weeds, the improvement which comprises also applying a carbamate selected from the group consisting of

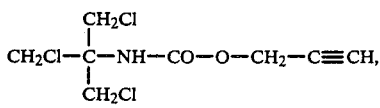

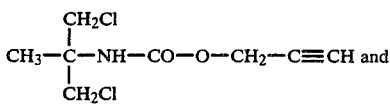

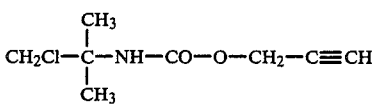

in an amount sufficient to synergize with the metribuzin and at a weight ratio of 1:3 to 20:1 based upon carbamate to metribuzin.

2. A process according to claim 1, wherein the carbamate is

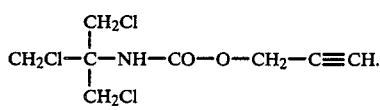

3. A process according to claim 1, wherein the carbamate is

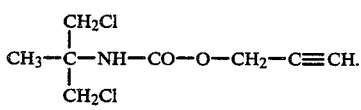

4. A process according to claim 1, wherein the carbamate is

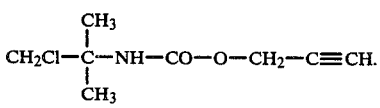

5. A synergistic herbicidal composition comprising a herbicidally effective amount of metribuzin and a synergistically effective amount of a carbamate selected from the group consisting of

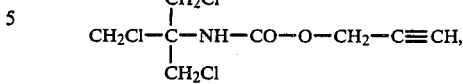

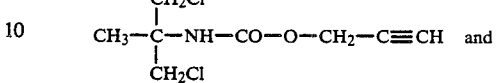

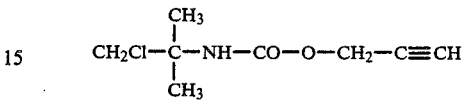

in an amount sufficient to synergize with the metribuzin and at a weight ratio of 1:3 to 20:1 based upon carbamate to metribuzin.

6. A composition according to claim 5, wherein the carbamate is

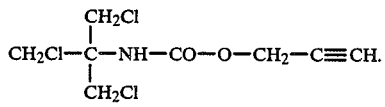

7. A composition according to claim 5, wherein the carbamate is

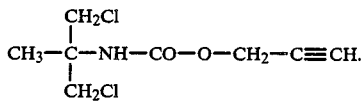

8. A composition according to claim 5, wherein the carbamate is

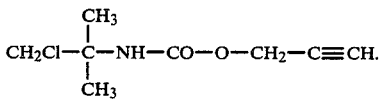

* * * * *

UNITED STATES PATENT AND TRADEMARK OFFICE
CERTIFICATE OF CORRECTION

PATENT NO. : 4,721,523

DATED : January 26, 1988

INVENTOR(S) : Michael Schwamborn, et al

It is certified that error appears in the above-identified patent and that said Letters Patent is hereby corrected as shown below:

Col. 14, line 36  Delete "urea" and substitute --area--

Col. 14, line 56, last col. heading; Col. 16, line 2, Col. 18, line 2, Col. 20, line 2 and Col. 22, line 2  Delete "hederacea" and substitute --Hederacea--

Col. 21, line 66  Delete "$n_{66D}{}^{20}$" and substitute --$n_D{}^{20}$--

Col. 22, line 53  Delete "$n_D{}^2$" and substitute --$n_D{}^{20}$--

Col. 25, line 1  Delete "Listed" and substitute --listed--

Col. 29, line 62  Delete "drop" and substitute --crop--

Signed and Sealed this

Twenty-ninth Day of November, 1988

*Attest:*

DONALD J. QUIGG

*Attesting Officer*  *Commissioner of Patents and Trademarks*